US00PP09923P

United States Patent [19]

van Geest

[11] Patent Number: Plant 9,923

[45] Date of Patent: Jun. 10, 1997

[54] FICUS VARIETY PLANT NAMED 'MELANY'

[75] Inventor: Jan van Geest, Gravenzande, Netherlands

[73] Assignee: The Plantenkwekerij P. Van Geest B.V., Netherlands

[21] Appl. No.: 582,513

[22] Filed: Jan. 3, 1996

[51] Int. Cl.[6] ..... A01H 5/00

[52] U.S. Cl. ..... Plt./88.9

[58] Field of Search ..... Plt./88.9

*Primary Examiner*—James R. Feyrer

*Attorney, Agent, or Firm*—Christie, Parker & Hale, LLP

[57] ABSTRACT

A variety of *Ficus elastica* having small glossy leaves, compact growth habit, and short internode length.

1 Drawing Sheet

BACKGROUND OF THE INVENTION

The present invention relates to a new and distinct cultivar discovered as a mutation in a controlled planting of *Ficus elastica* 'Decora' in a greenhouse in s, Gravenzande, The Netherlands, The varietal denomination of the new cultivar is 'Melany'.

SUMMARY OF THE INVENTION

'Melany' is a mutation of the variety *Ficus elastica* 'Decora'. The new variety has been asexually reproduced by rooted cuttings in s, Gravenzande, The Netherlands. Asexual reproduction through succeeding generations has established that the combination of characteristics as herein disclosed for the new cultivar are firmly fixed and retained through successive generations of asexual reproduction. Various methods of asexual reproduction, such as micropropagation, layering and reproduction from vegetative cuttings, may be used to reproduce the new variety.

Comparison with Parent and Other Varieties

In the description herein, color references are to The Royal Horticultural Society Colour Chart (RHSCC). The terminology used in the color descriptions herein refers to plate numbers in this color chart.

'Melany' is distinguishable from 'Decora' by, among other features, its compact growth habit and internode spacing. Whereas internode spacing of 'Decora' is about 5.5 cm, internode spacing of 'Melany' is about 2 cm. In addition, the leaves of 'Melany' are much smaller than 'Decora' and are substantially more glossy. Mature leaves of 'Melany' are about 15×7 cm on average as compared to 'Decora' which is about 25×15 cm on average.

Young leaves of 'Melany' emerge with a reddish green-brown color, which may also be described as greenish-burgundy, in contrast to the young leaves and mature foliage of 'Decora' which is a lighter green, near 138A. The RHS color chart does not have a color that matches the greenish-burgundy, but the color combination of 166A mixed with 147A would most closely resembly the color of the young leaves. Upon microscopic examination, it is evident that the lamina of the upper sides of the leaves is green, close to RHS 147A. The minute venation coloration is close to RHS 166A. This veination gives a reddish cast to the leaves. As the leaves mature, the veination becomes less evident and the dark green color becomes the predominant color of the upper side of the leaves.

The leaves of 'Melany' are very highly glossy, so glossy as to be described as appearing as if they had been sprayed with oil. Within approximately 2 weeks, the young leaves mature and become more rigid. As they mature, the color of the mature leaves changes to a deep green closely resembling RHS 139A. The color of the young leaves as well as the mature foliage of the parent plant is a light green, close to RHS 138A.

Other differences exist in connection with the mid-rib veins. 'Melany' has a pronounced, thin, single mid-rib vein on the upper side of the leaf (approximately 2 mm in width measured at the base of the leaf next to the petiole) which runs from the petiole to the cuspidate leaf tip. This mid-rib vein is generally pink in color on juvenile leaves as well as young mature leaves. On older mature leaves (leaves that have been on the plant more than approximately 12 weeks), the mid-rib vein lightens to a lime green color with a light dusting of pink coloration, near 139C. The pronounced convex mid-rib vein on the underside of the leaf of 'Melany' is a creamy olive green color, near 138B. In contrast, 'Decora' has a thick mid-rib vein (approximately 5 mm measured at the base of the leaf next to the petiole) that runs from the petiole to the cuspidate leaf tip which is a light cream color on the upper side of the leaf. The cream color on the upper side of the mid-rib vein of 'Decora' is close to 19B and this coloration has been observed on young leaves as well as mature foliage. However, the underside of leaves of 'Decora' the convex mid-rib vein is a pink color, near 179C.

Although the upper side of the leaves of 'Decora' have a concave surface, the upper side of leaves of 'Melany' is slightly convex. The 'Melany' cuspidate leaf curls downward slightly and the margins of the outer lamina of the leaves curl downward as well as creating a convex upper side on the leaf's surface. The upper side of 'Decora' is smooth and without ridges.

In addition to the foregoing, the upper side leaf surface of 'Melany' has ridges that radiate from the central mid-rib vein to the outer margin of the leaf angling off from the mid-rib vein at approximately 60° angle and arc spaced at approximately 5 mm apart. These convex ridges distinguish 'Melany' visually and cause the already glossy lamina of the leaves to reflect more light which visually accentuates the highly glossy surface of the leaves of the new variety. When viewing the underside of the leaves of 'Melany' and that of its parent, it is evident that the ridges on the upper leave side of 'Melany' are due to prominent secondary veination in the leaves. Viewing the underside of its parent, for comparison, shows that the secondary veination on 'Decora' is not a significant feature and does not create a ridging affect on the upper side, rather, the leaf of 'Decora' is smooth on the upper side.

Also, as previously mentioned, the underside of the leaf of 'Melany' is somewhat glossy whereas the underside of the leaf of 'Decora', when compared side-by-side, has a notable absence of gloss and may be described as having a matte finish. There is a very noticeable increased glossiness of the leaves of 'Melany' when compared to those of 'Decora'.

BRIEF DESCRIPTION OF THE ILLUSTRATION

The accompanying illustration shows a specimen of the new cultivar true to color as in reasonably possible to make in an illustration of this character, showing a plant in a 23 cm nursery pot and having an overall height of about 76 cm.

DESCRIPTION OF THE NEW VARIETY

'Melany' has not been observed under all possible environmental conditions. The phenotypic expression may vary with variations in environment such as temperature, light intensity, day length, fertilizer rates and other cultural conditions.

The following observations and descriptions are of plants grown in under glass in the Netherlands.

Classification:

*Botanical.—Ficus elastica* 'Melany'.

Parentage: Mutation of *Ficus elastica* 'Decora'.

Propagation: By vegetative cuttings, air layering, micropropagation and other known asexual reproduction techniques.

PLANT

A. Form: Upright, glabrous highly glossy and richly branching with a very compact growth pattern and short internode spacing.

B. Leaves:

1. *Form.*—Oblong, elliptical, medium sized leaf with a cuspidate leaf tip.
2. *Size.*—On average, the leaves are 15 cm long by 7 mm wide.
3. *Margins.*—Smooth.
4. *Texture.*—Ridged, very highly glossy, and glabrous.
5. *Petiole.*—About 1.5 cm long.
6. *Variegation.*—None.
7. *Quantity.*—Multiple, numerous and alternating, with an average of 8 mature leaves per 10 cm of stem.
8. *Color.*—Upper surface mature leaves near 139A; upper surface young leaves near 166A in combination with near 147A; under surface mature leaves near 137B; under surface young leaves near 137C. It should be noted that due to the vascularity (venation) on the under sides of the leaves there is a reddish cast to the leaves that overlays the green lamina. This is due to the numerous capillaries in the leaf which upon close examination are red in color, near 180A.
9. *Auricle.*—Absent.

C. Wood: Because 'Melany' is a commercially produced plant and is most aesthetically pleasing when the plants are relatively young, 'Melany' has not been observed in a sufficiently mature enough state as to be able to make observations on the wood. *Ficus elasticas* are not a very woody type of Ficus when cultivated in the greenhouse, however, they do eventually produce wood when they are grown outdoors in tropical and sub-tropical environment. To date, Ficus 'Melany' has not been cultivated outdoors under these conditions, therefore, the formation of wood on the plant has not been observed.

D. Pests and diseases: 'Melany' appears to be no more or any less susceptible to the common pests that affect other *Ficus elasticas,* including, scales, mealy bugs, thrips and mites. Because the greenhouses in The Netherlands are sprayed prophylactically on a regular basis to control a number of insects and diseases, very few pests or diseases have been observed on the Ficus 'Melany'.

E. Temperature range: To 0° C.; preferred growing temperatures are about 20° to 32° C., with a light intensity of about 5,000 fc.

F. Stipules: Large pointed sheaths approximately 16 cm long that are a light shade of red-brown; they unfurl and quickly wither and fall away to exfoliate as the new leaf emerges.

G. Inflorescence: To date, Ficus 'Melany' has not born fruit or flowers.

I claim:

1. A new and distinct variety of *Ficus elastica* plant named 'Melany', substantially as illustrated and described.

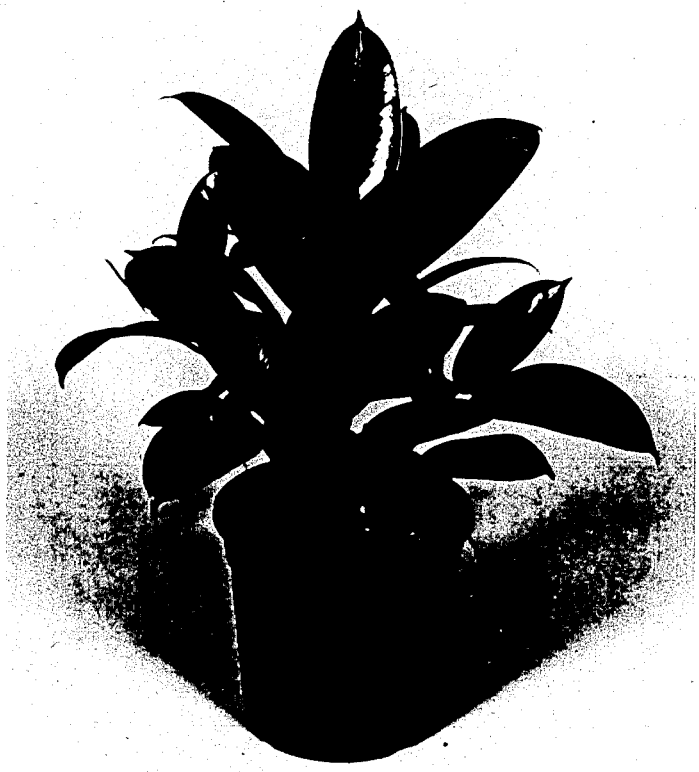

* * * * *